(12) United States Patent
Damarati

(10) Patent No.: US 8,936,610 B2
(45) Date of Patent: *Jan. 20, 2015

(54) MULTIPLE HEMOCLIP SYSTEM FOR AN ENDOSCOPE

(75) Inventor: John J. Damarati, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/369,503

(22) Filed: Feb. 9, 2012

(65) Prior Publication Data

US 2012/0136376 A1    May 31, 2012

Related U.S. Application Data

(63) Continuation of application No. 11/773,936, filed on Jul. 5, 2007, now Pat. No. 8,133,240, which is a continuation of application No. 11/351,294, filed on Feb. 9, 2006, now abandoned, which is a continuation of application No. 10/723,433, filed on Nov. 26, 2003, now Pat. No. 7,001,399, which is a continuation of application No. 10/281,900, filed on Oct. 24, 2002, now Pat. No. 6,679,894.

(60) Provisional application No. 60/347,832, filed on Oct. 24, 2001.

(51) Int. Cl.
*A61B 17/10* (2006.01)
*A61B 17/122* (2006.01)
*A61B 17/128* (2006.01)
*A61B 17/00* (2006.01)
*A61B 17/29* (2006.01)

(52) U.S. Cl.
CPC ............ *A61B 17/122* (2013.01); *A61B 17/1227* (2013.01); *A61B 17/1285* (2013.01); *A61B 2017/00867* (2013.01); *A61B 2017/2905* (2013.01); *A61B 2017/2924* (2013.01)
USPC ........................................................ 606/143

(58) Field of Classification Search
USPC ......................................... 606/108, 142, 143
See application file for complete search history.

(56) References Cited

U.S. PATENT DOCUMENTS

| | | | |
|---|---|---|---|
| 4,451,256 A * | 5/1984 | Weikl et al. | 604/164.03 |
| 4,484,911 A * | 11/1984 | Berlin et al. | 604/174 |
| 5,395,381 A * | 3/1995 | Green et al. | 606/143 |
| 5,766,163 A * | 6/1998 | Mueller et al. | 606/7 |
| 6,306,149 B1 * | 10/2001 | Meade | 606/143 |
| 6,352,541 B1 * | 3/2002 | Kienzle et al. | 606/143 |
| 6,824,547 B2 * | 11/2004 | Wilson et al. | 606/143 |

* cited by examiner

Primary Examiner — Katherine Dowe
(74) Attorney, Agent, or Firm — Fay Kaplun & Marcin, LLP

(57) ABSTRACT

Spring clips are arranged end to end in a cavity of an inner shaft. Such shaft slides within an outer shaft, and a pusher member slides in the cavity behind the clips. The clips have jaws biased together, but which are wedged apart by an opener as the pusher is moved distally. An opened clip is ejected by relative movement of the inner and outer shafts to clamp body tissue at a desired site.

20 Claims, 5 Drawing Sheets

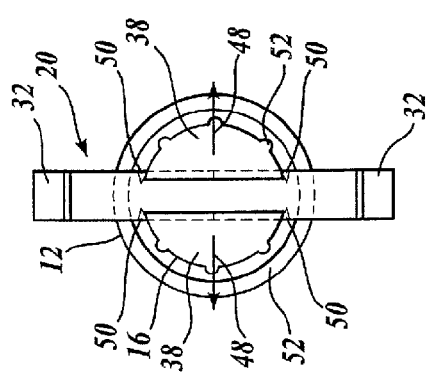
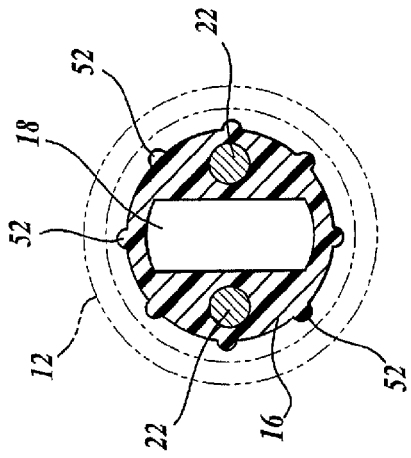
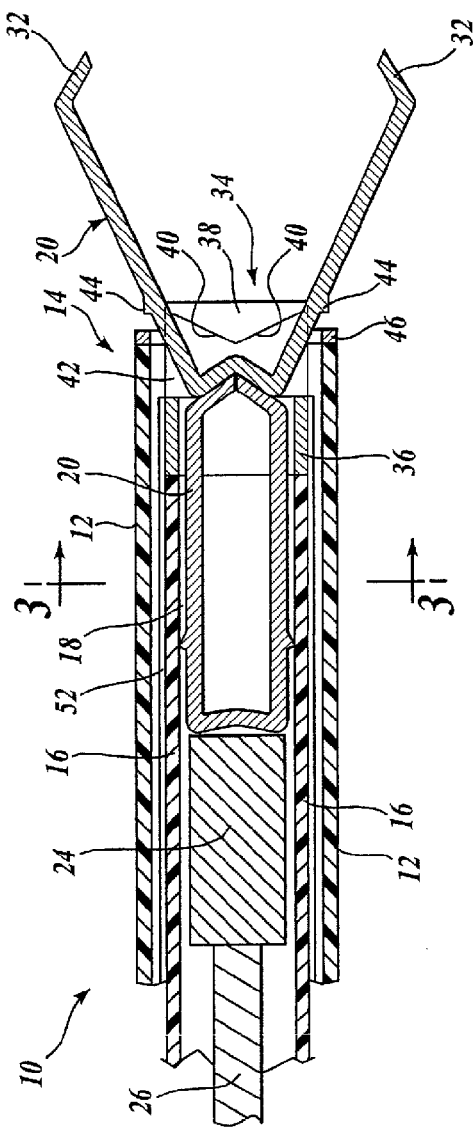
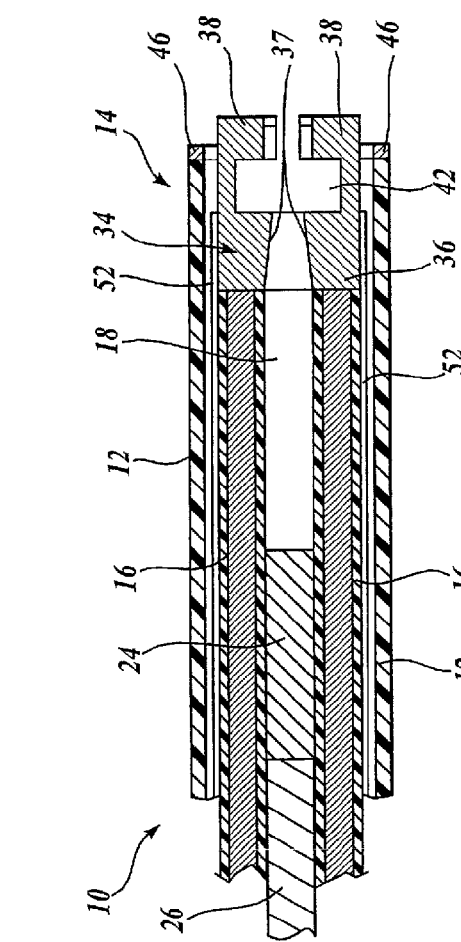

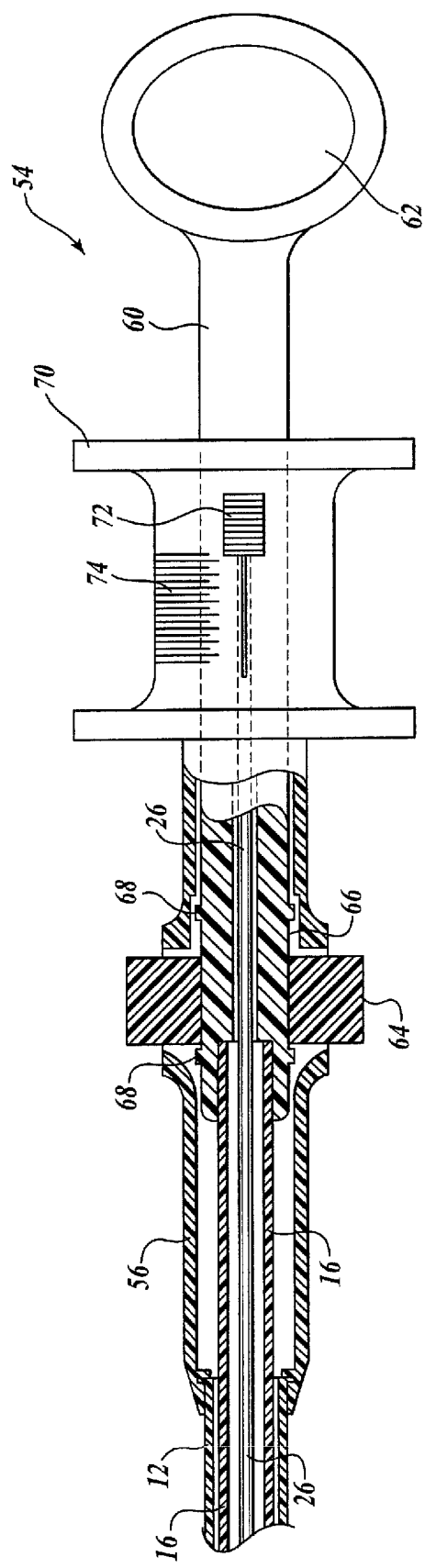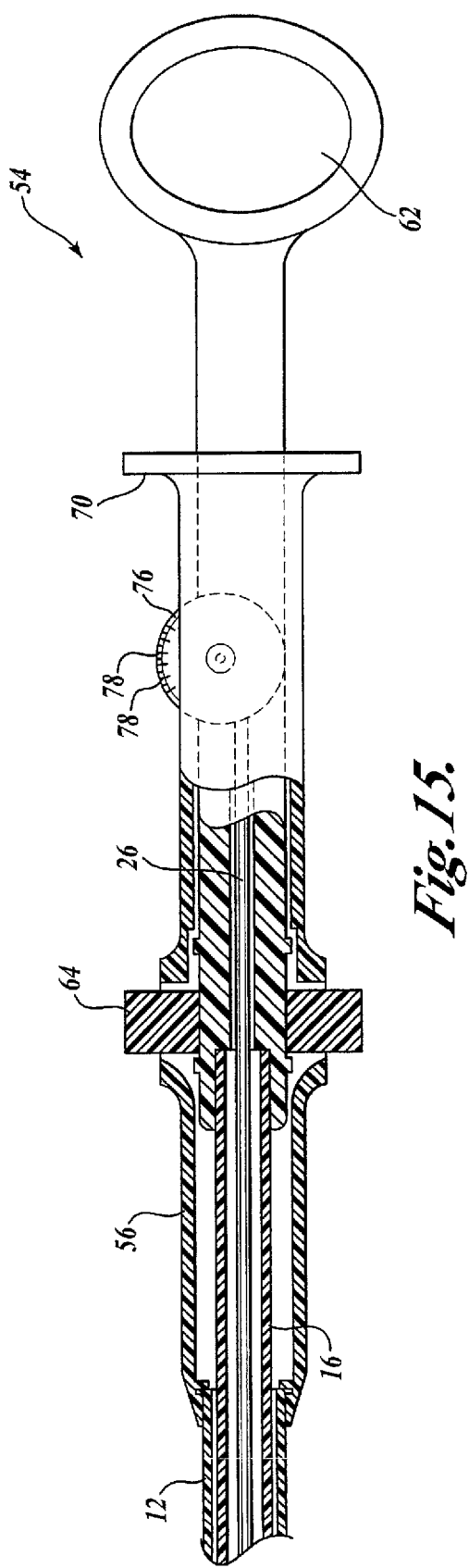

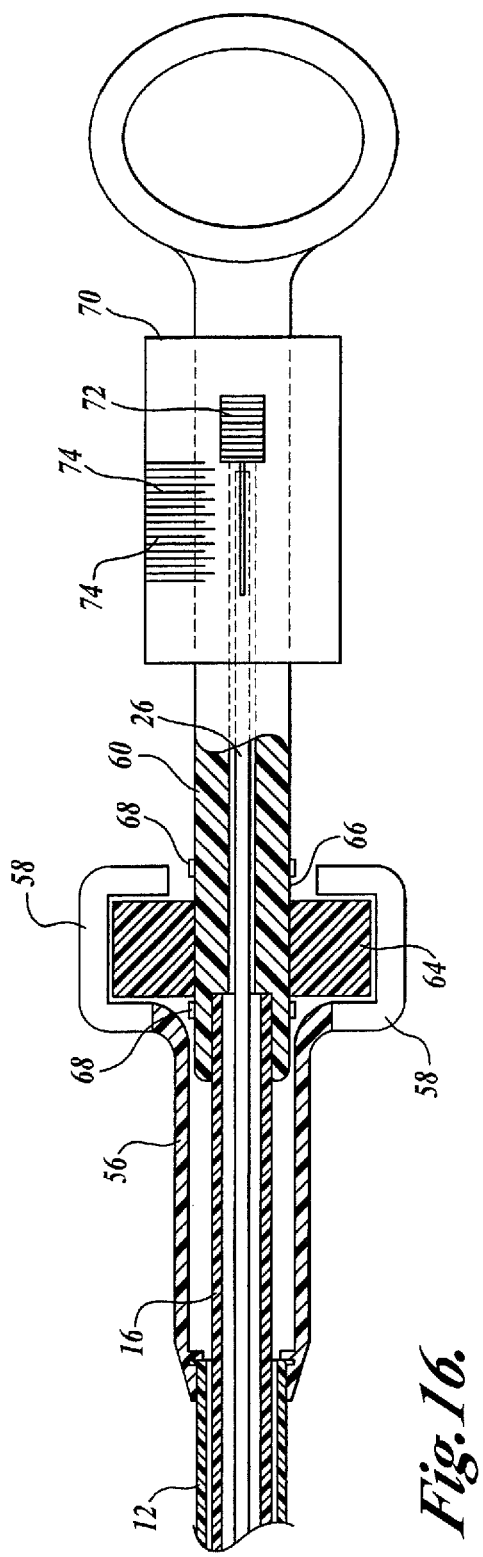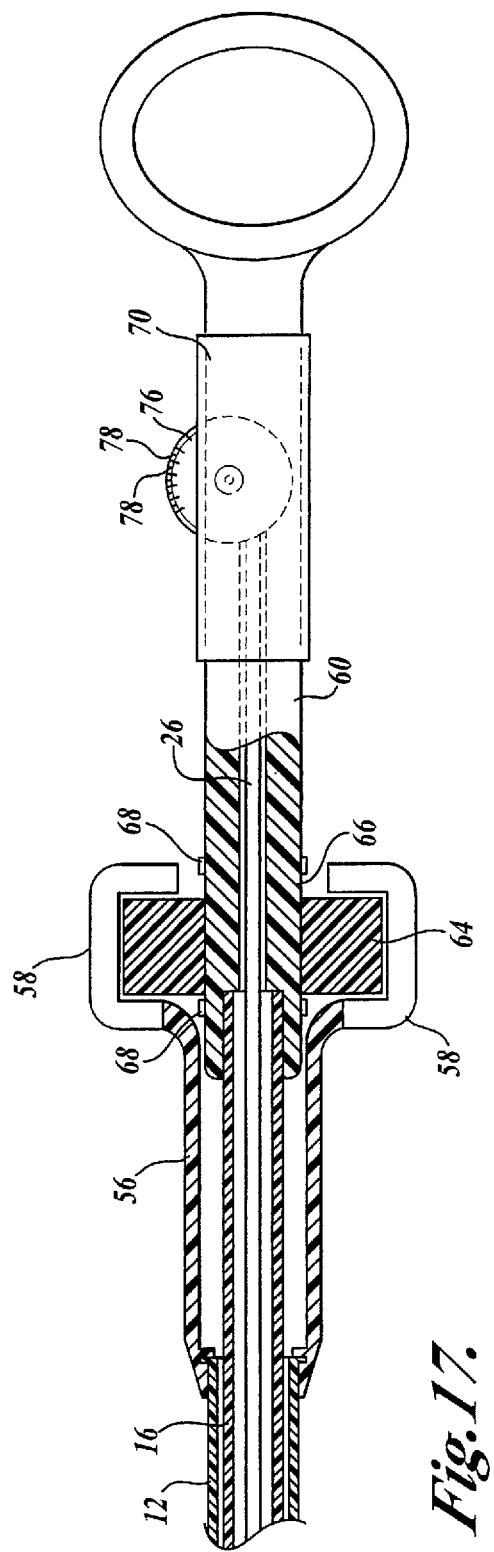

MULTIPLE HEMOCLIP SYSTEM FOR AN ENDOSCOPE

CROSS-REFERENCES TO RELATED APPLICATIONS

This application is a which is Continuation application of U.S. patent application Ser. No. 11/773,936 filed on Jul. 5, 2007, now U.S. Pat. No. 8,133,240; which is a Continuation application of U.S. patent application Ser. No. 11/351,294 filed on Feb. 9, 2006 (now abandoned); which is a Continuation application of U.S. patent application Ser. No. 10/723,433 filed on Nov. 26, 2003 (now U.S. Pat. No. 7,001,399) which is a Continuation application U.S. patent application Ser. No. 10/281,900 filed on Oct. 24, 2002 (now U.S. Pat. No. 6,679,894), which claims priority to U.S. Provisional Patent Application Ser. No. 60/347,832 filed on Oct. 24, 2001. All applications/patents are expressly incorporated herein, in their entirety, by reference.

FIELD OF THE INVENTION

The present invention relates to a system for clipping body tissue, such as a system for introducing a clip for hemostasis ("hemoclip") endoscopically in the GI tract.

BACKGROUND OF THE INVENTION

One known system for introducing a hemoclip endoscopically is shown in U.S. Pat. No. 3,958,576 assigned to Olympus Optical Co. Ltd. of Japan. See also Japanese Patent Publication No. 04102450 and U.S. Pat. No. 5,766,189. Each of these devices is used to insert a single clip, and includes a series of mechanical members to insert, eject and close or clamp the clip at a desired location, such as for hemostasis in the GI tract.

SUMMARY OF THE INVENTION

The present invention provides an improved hemoclip system. In one aspect of the invention multiple clips can be applied internally by way of a conventional endoscope without removal and reinsertion of a clip-retaining member. The system provides good control of the rotated position of a clip, with little backlash, for convenient and reliable placement of a clip or clips.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is an enlarged side elevation of the distal portion of a multiple hemoclip system for an endoscope in accordance with the present invention with parts shown in section;

FIG. 2 is a distal end elevation of the device of FIG. 1;

FIG. 3 is a transverse section along line 3-3 of FIG. 1, with parts removed;

FIG. 4 is a top plan of the distal end portion of the device with parts shown in section;

FIG. 14 is a top plan of a second embodiment of a proximate portion of a multiple hemoclip system in accordance with the present invention, with parts broken away;

FIG. 15 is a top plan of a third embodiment of a proximate portion for a system in accordance with the present invention, with parts broken away;

FIG. 16 is a top plan of a fourth embodiment of proximate portion for a system in accordance with the present invention, with parts broken away; and FIG. 17 is a top plan of a fifth embodiment of a proximate portion for a system in accordance with the present invention, with parts broken away.

DETAILED DESCRIPTION OF THE PREFERRED EMBODIMENT

Figure 5:
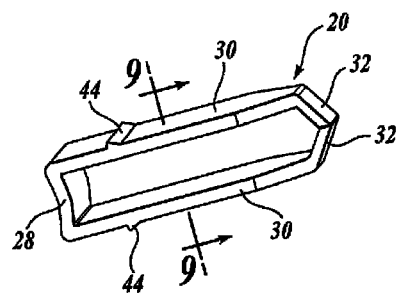
FIG. 5 is a top perspective of a hemoclip usable in the system of the present invention.

With reference to FIGS. 1-4, a hemoclip system 10 in accordance with the present invention includes an elongated outer tube or shaft 12 which may be inserted through a conventional scope for positioning a distal, clip-carrying portion 14 of the shaft at a desired location of the body, such as a location of bleeding to be clamped. Such elongated outer tube or shaft 12 can be manufactured from an extruded biocompatible polymer or other suitable material. The proximate end portion of the outer shaft connects to a handle as described below with reference to FIGS. 12-17 for external control of the relatively movable component parts of the distal portion 14.

An inner shaft 16 is slideably received within the outer shaft 12, and also may be manufactured from an extruded biocompatible polymer or other suitable material. The longitudinal position of the inner shaft 16 relative to the outer shaft 12 can be adjusted.

The cross-sectional shape of the major portion of the inner shaft 16 is best seen in FIG. 3. A generally rectangular bore or cavity 18 is sized for receiving spring clips 20 of the type described in more detail below. To prevent stretching of the inner shaft, support wires 22 can be embedded in it at opposite sides of the central cavity or recess 18.

The cavity 18 is shaped for reception of spring clips 20. Such clips fit close within the cavity 18 but are freely slideable therein. In general, several clips are preloaded in the distal end of the inner shaft, such as three or more clips placed end to end. The clips are dispensed, in part, by a pusher block 24 received in the recess 18 proximate to the clips. The pusher block can be moved distally and proximally by manipulation of an attached core wire 26. Wire 26 extends through the inner shaft 16 and is slidable therein.

The clips 20 can be manufactured from a metal with spring and/or memory properties, such as stainless steel or Nitinol. With reference to FIG. 5, the basic shape is a thin band plate, bent toward its center or web 28 to form a long U with elongated opposing jaws 30. The ends of the jaws are bent inward to form teeth 32 that face each other. The inner ends of the teeth can be sharpened to form grabbing hooks.

Returning to FIGS. 1 and 2, a clip opener component 34 is secured at the distal end of the inner shaft 16, such as by attachment to the strengthening wires 22 (shown in the cross-section of FIG. 3). Such wires preferably extend the full length of the inner shaft. The clip opener includes a continuous shell 36 at its proximate end and two side pieces 38 at its distal end. As seen in FIG. 4, the proximate portion or shell 36 tapers inward at opposite sides 37 (this tapering and other dimensions are exaggerated in the drawings for ease of illustration and description). The distal or leading ends of the clip jaws are similarly tapered. A clip 20 is "loaded" by forcing it forward, using the pusher block 24. This has the effect of wedging the side pieces 38 apart until the proximate or trailing end of the clip clears the tapered sides 37. After a short travel of the clip distally, the opening between the clip jaws formed by the teeth 32 engage the distal end portions of the side pieces 38 which project part way into the path that a clip follows when driven forward by the clip pusher 24. See, for example, the position of the side pieces 38 in FIG. 2. The adjacent edges of the side pieces 38 are spaced apart transversely but are close enough together so as to be engaged by the tapered leading ends of the clip 20. Each side piece has proximate wedge surfaces 40 (FIG. 1) angled outward from the center line of the device and configured such that the distal ends of the clip jaws are wedged apart when the pusher block moves the clip against the opener surfaces 40. Consequently, as a clip is forced forward along the cavity 18 of the inner shaft 16, the clip teeth 32 and jaws 30 are wedged apart to the condition illustrated at the right of FIG. 1, contrary to the natural memory or spring characteristics of the clip. This action tends to spread the side pieces 38 apart until the central portion or web 28 of the clip fits within an intermediate cavity portion 42 of the clip opener 34. When this position is reached, the clip is reliably held in the clip opener with its jaws open.

The opened clip can be moved by manipulation of the outer shaft or tube 12, and can be rotated by manipulation of the inner tube or shaft 16. When a desired site and orientation are reached, such as a bleeding site, the clip can be ejected by withdrawing the inner shaft 16 relative to the outer shaft 12. With reference to FIG. 1, projections 44 on the outer sides of the clip jaws 30 are positioned to engage against a metal collar 46 provided at the end of the outer shaft 12. With reference to FIG. 2, as the inner shaft, including clip opener 34, is retracted within the outer tube, the opener side pieces 38 are wedged apart, in the direction of the arrows 48. In addition, the clip edges can have weakening nicks 50 (shown only in FIG. 2) that allow the metal of the jaws to bend inward as the jaws move past the opener side pieces 38, until the clip is released and its teeth 32 move toward each other to clamp the tissue at the desired site, due to the inherent spring or memory characteristics of the clip. After dispensing of one clip, the next clip can be moved into position by manipulation of the core wire 26 and attached pusher 24.

With reference to FIG. 3, the outer periphery of the inner shaft 16 can have equally spaced ribs 52 for ease in sliding along the inner periphery of the outer shaft 12. The shafts and core wire 26 can be curved or bent during use, depending on the application.

Figure 8:
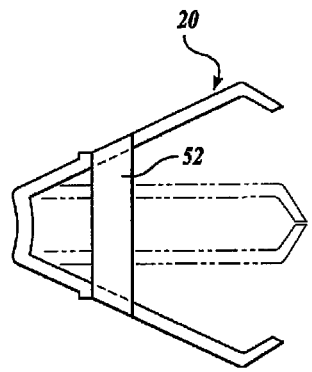
FIG. 8 is a side elevation of a fourth embodiment of a hemoclip usable in the system of the present invention.
Figure 6:
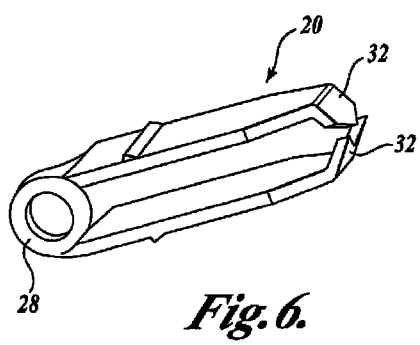
FIG. 6 is a top perspective of a second embodiment of a hemoclip usable in the system of the present invention.
Figure 9:
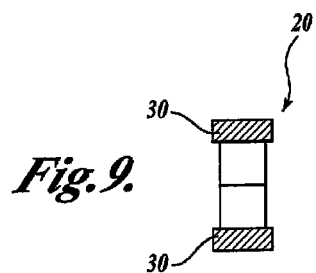
FIG. 9 is a vertical section along line 9-9 of FIG. 5.
Figure 7:
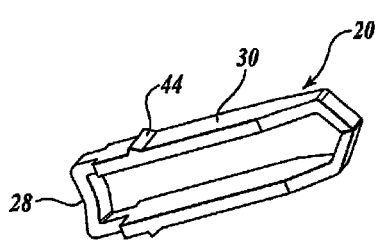
FIG. 7 is a top perspective of a third embodiment of a hemoclip usable in the system of the present invention.
Figure 10:
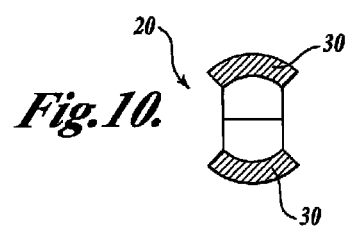
FIG. 10 is a vertical section corresponding to FIG. 9 showing aspects of an alternative embodiment of a hemoclip usable in the system of the present invention.
Figure 11:
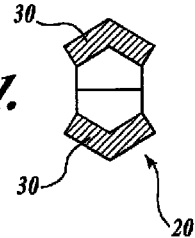
FIG. 11 is a vertical section corresponding to FIG. 9 showing aspects of a further embodiment of a hemoclip usable in the system of the present invention.

Different clip geometries may be used, as illustrated in FIGS. 5-11. Preferably the clips are quite wide, at least one millimeter, for maximum spring force. With reference to FIG. 6, one of the teeth 32 can form a sharpened angular projection shaped to be received in a corresponding angular recess of the other tooth 32. The web end 28 of the clip can include a circular or helical wire spring member. With reference to FIG. 7, the web portion 28 of the clip can be narrower than the main body portion of the jaws 30, to allow some pivoting movement of an open clip when in the position at the right of FIG. 2, it being understood that the narrowed portion of the clip web 28 would extend beyond the distal end of the outer shaft. In that case, the shoulders formed between the web 28 and jaws 30 could be positioned to substitute for the projections 44. With reference to FIG. 8, closing force for the clip 20 can be achieved or augmented by a separate elastic band 52. One or more of the clip components can be bioabsorbable, so that the clip would automatically be released over time. The clip jaws 30 can be of rectangular cross-section (FIG. 9) or can be arcuate (FIG. 10) or angled (FIG. 11) for increased rigidity.

Figure 12:
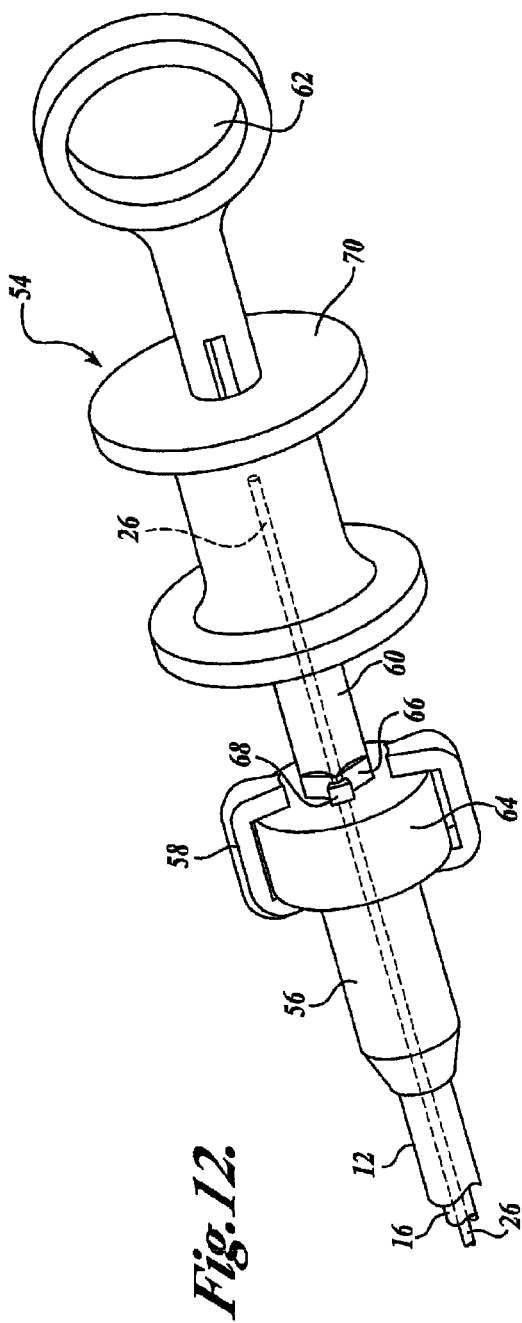
FIG. 12 is a diagrammatic top perspective of the proximate portion of a multiple hemoclip system for an endoscope in accordance with the present invention.
Figure 13:
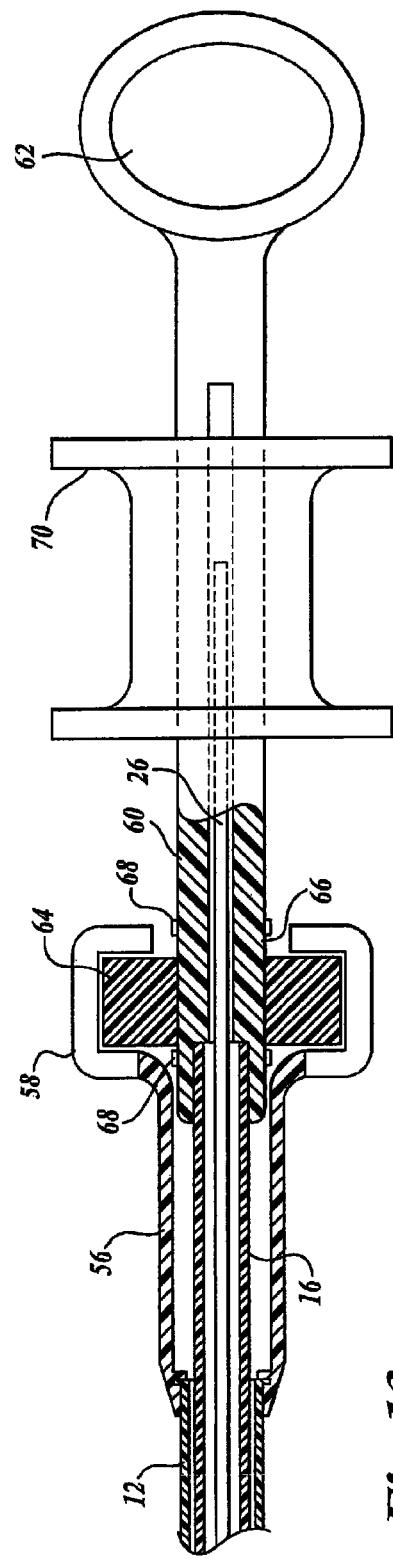
FIG. 13 is a side elevation of the proximate portion shown in FIG. 12, with parts broken away.

With reference to FIGS. 12 and 13, the proximate portion 54 of the multiple hemoclip system in accordance with the present invention can be in the form of a handle having separate components for positioning the outer shaft 12 and manipulating the inner shaft 16 and core wire 26 connected to the clip opener and pusher, respectively. The parts are shown diagrammatically. The outer shaft 12 is coupled to a larger fitting 56 leading to a bracket portion 58 that can more easily be grasped and positioned by a user. The inner shaft 16 is coupled to a proximate extension 60 leading to a finger hole 62. Most of the extension 60 is cylindrical, but an operating knob 64 is journaled on a short noncylindrical portion 66 of the extension. The knob can be turned to rotate the inner shaft, but is slideable along the noncylindrical portion 66. Sliding movement of the extension relative to the knob 64 is limited by stops 68 at both sides. Since the knob is held within the bracket 58, stops 68 define the maximum travel of the inner shaft 16 inside the outer shaft 12.

The core wire 26 is coupled to a sliding spool 70. The spool is moveable fore and aft (distally and proximally) along the extension 60, for moving the core wire and attached clip pusher relative to the inner shaft 16. Thus, the proximate portion 54 can be manipulated to position a clip adjacent to a site to be clamped, whereupon the spool 70 is moved distally to slide the core wire 26 and clip pusher 24 sufficiently to position the distal most clip as shown at the right of FIG. 1. Knob 64 can be used to rotate the inner shaft to orient the clip as desired. Only a short relative movement of the inner and outer shafts is required to eject the clip, which will relax toward its closed position to apply a clamping force at the desired site. Thereafter, the device need not be removed and reloaded. Rather, the next clip can be moved forward and the process repeated to secure another clip. Removal of the distal portion of the multiple hemoclip system is not required until the supply of preloaded clips has been exhausted.

Other proximate operating mechanisms can be used. In the embodiment of FIG. 14, the inner shaft 16 is coupled to the long, cylindrical extension 60 leading to the finger hole 62, as in the previously described embodiment. Also, knob 64 is journaled on, and slideable along, the non-circular portion 66, with such sliding movement being limited by stops 68. However, in the embodiment of FIG. 14, the fitting 56 continues to and is affixed to the spool 70. Knob 64 has opposite sides that project through openings in the fitting or housing 56. Relative movement of the extension 60, such as by use of the finger hole 62, and the spool 70 results in corresponding relative movement of the inner shaft 16 and outer shaft 12.

In the embodiment of FIG. 14, the core wire 26 connects to a slide mechanism having an external operating button 72 slideably mounted on the spool structure 70. Indicia 74 adjacent to the button 72 indicate the position of the pusher block carried by the core wire 26 at its distal end. Thus, by viewing the position of the button 72 relative to the indicia 74, a user will know the position of the clips at the distal end and also the number of clips remaining.

The embodiment of FIG. 15 is identical to the embodiment of FIG. 14 except for the mechanism for moving the core wire 26. In this embodiment, the spool portion 70 carries a rotatable dial 76 having indicia 78. The core wire 26 connects to or is wrapped around an internal segment of the dial such that rotation of the dial moves the core wire 26 (and attached clip pusher) inside the inner shaft 16. The indicia 78 can be used to determine the position of the clips at the distal end and/or the number of clips remaining to be dispensed.

In the embodiments of FIGS. 16 and 17, the fitting 56 connected to the outer shaft 12 is identical to that used in the embodiment of FIGS. 12 and 13, including the bracket portions 58. In addition, the inner shaft 16 connects to the extension 60, with a non-circular segment 66 on which the knob 64 is journaled, and stops 68 limiting the relative movement of the inner and outer shafts. In the embodiment of FIG. 16, however, the spool section 70 is fixed to the extension 60. Core wire 26 is moved relative to the spool (and, consequently, relative to the inner shaft) by a slide operating mechanism of the type described above with reference to FIG. 14. The external button 72 is slideable lengthwise of component 70 for moving the core wire 26, and indicia 74 can be used to determine the position of the clips and the number of clips remaining.

The embodiment of FIG. 17 is identical to the embodiment of FIG. 16 except for the mechanism for moving the core wire 26. In the FIG. 17 embodiment, a dial mechanism of the type described above with reference to FIG. 15 is used. Component 70 is fixed to the inner shaft extension 60. Indicia 78 on the dial 76 indicate the position of the clips and the number of clips remaining.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A tissue clipping device, comprising:
    an elongated first shaft extending from a proximal end connected to a handle to a distal end and including a first channel extending therethrough;
    an elongated second shaft extending from a proximal end to a distal end and including a second channel extending therethrough, wherein the second shaft is positioned within the first shaft;
    a U-shaped clip having first and second jaws movable between an open configuration in which the first and second jaws are moved radially away from one another to capture a portion of tissue therebetween and a closed configuration in which the first and second jaws are moved radially toward one another, the clip being biased toward the closed configuration;
    a pusher element enclosed within the second channel proximally of the clip to control distal longitudinal movement of the clip therewithin;
    a clip opening element adjacent a distal end of the second shaft, the clip opening element comprising an elongated shell having first and second side arms extending distally therefrom and including tapered surfaces contacting distal ends of the first and second jaws to move the clip from the closed configuration to the open configuration; and
    a core wire a distal end of which is connected to a proximal portion of the pusher element to control movement thereof, the distal end of the core wire being housed within the second channel.

2. The device of claim 1, wherein a cross-sectional shape of the second channel is substantially rectangular.

3. The device of claim 1, wherein the second shaft comprises a first support wire embedded therewithin.

4. The device of claim 3, wherein the second shaft comprises a second support wire embedded therewithin on an opposing side of the first support wire relative to the second channel.

5. The device of claim 1, wherein the second shaft is longitudinally slidable relative to the first shaft to control a movement of the clip.

6. The device of claim 1, wherein the second shaft is rotatable relative to the first shaft to control a rotational orientation of the clip.

7. The device of claim 1, wherein an outer surface of the second shaft is ribbed.

8. The device of claim 1, wherein the first and second shafts are formed of a biocompatible polymer.

9. The device of claim 1, wherein the core wire is connected to an actuation mechanism provided on the handle.

10. The device of claim 1, wherein distal ends of the first and second jaws comprise teeth sharpened to form hooks.

11. The device of claim 1, wherein a proximal portion of the shell is tapered.

12. The device of claim 1, further comprising a web joining proximal ends of the first and second jaws to one another.

13. The device of claim 12, wherein the web is one of planar, circular and helical.

14. The device of claim 1, further comprising a removable elastic band provided over the first and second jaws to maintain the clip in the closed configuration.

15. A tissue clipping system, comprising:
    an elongated first shaft extending from a proximal end connected to a handle to a distal end and including a first channel extending therethrough;
    an elongated second shaft extending from a proximal end to a distal end and including a second channel extending therethrough, wherein the second shaft is positioned within the first shaft;
    a plurality of U-shaped clips housed in the second channel, each having first and second jaws movable between an open configuration in which the first and second jaws are moved radially away from one another to capture tissue positioned therebetween and a closed configuration in which the first and second jaws are moved radially toward one another to grip tissue therebetween, the clips being biased toward the closed configuration;
    a pusher element enclosed within the second channel proximal of a proximal-most one of the clips and configured to control distal longitudinal movement of the proximal-most clip therewithin;
    a clip opening element adjacent a distal end of the second shaft, the clip opening element comprising an elongated shell having first and second side arms extending distally therefrom and including tapered surfaces contacting distal ends of the first and second jaws of a distal-most one of the clips to move the distal-most clip from the closed configured to the open configuration; and
    a core wire a distal end of which is connected to a proximal portion of the pusher element to control movement thereof, a distal end of the core wire being housed within the second channel.

16. The system of claim 15, wherein the core wire is connected to an actuation mechanism provided on the handle.

17. A method, comprising:

inserting a distal portion of a tissue clipping device into a living body until distal ends of first and second elongated shafts are adjacent target tissue, the first shaft extending between a proximal end connected to a handle and a distal end and including a first channel extending therethrough, the second shaft extending within the first shaft from a second shaft proximal end to a second shaft distal end and including a second channel extending therethrough, wherein the second shaft is positioned within the first shaft;

operating a core wire, a distal end of the core wire is connected to a proximal portion of a pusher element to push a clip distally through the second channel until a distal end thereof contacts a tapered surfaces of a clip opening element attached to the distal end of the second shaft such that contact between the tapered surfaces and the distal ends of jaws of the clip spread the jaws apart to move the clip to an open configuration, the jaws being biased toward a closed configuration, wherein the pusher element is enclosed within the second channel proximally of the clip;

receiving the target tissue between the opposing jaws of the clip in the open configuration; and releasing the jaws of the clip to capture the target tissue therebetween.

18. The method of claim 17, further comprising rotating the second shaft relative to the first shaft to rotate the clip to a desired angular orientation.

19. The method of claim 17, further comprising the step of moving the second shaft proximally relative to the first shaft to deploy the clip from the tissue clipping device through a slotted opening defined between first and second side arms of the clip opening element.

20. The method of claim 17, further comprising the step of pivoting the clip in the open configuration to aid in positioning thereof over the target tissue.

* * * * *